US010456484B2

(12) United States Patent
Kemp et al.

(10) Patent No.: US 10,456,484 B2
(45) Date of Patent: Oct. 29, 2019

(54) STERILISATION CONTAINER, METHOD OF STERILISATION AND STERILISATION APPARATUS

(71) Applicant: Mercer Technologies Limited, Christchurch (NZ)

(72) Inventors: Terry Dean Kemp, Queensland (AU); Alan Reg Dowman, Auckland (NZ)

(73) Assignee: MERCER TECHNOLOGIES LIMITED, Christchurch (NZ)

( * ) Notice: Subject to any disclaimer, the term of this patent is extended or adjusted under 35 U.S.C. 154(b) by 0 days.

(21) Appl. No.: 15/510,835

(22) PCT Filed: Sep. 11, 2015

(86) PCT No.: PCT/NZ2015/050142
§ 371 (c)(1),
(2) Date: Mar. 13, 2017

(87) PCT Pub. No.: WO2016/039647
PCT Pub. Date: Mar. 17, 2016

(65) Prior Publication Data
US 2017/0258951 A1    Sep. 14, 2017

(30) Foreign Application Priority Data

Sep. 12, 2014 (NZ) ........................................ 631430
Sep. 12, 2014 (NZ) ........................................ 631431

(51) Int. Cl.
*A61L 2/07* (2006.01)
*A61L 2/26* (2006.01)
(Continued)

(52) U.S. Cl.
CPC ................ *A61L 2/07* (2013.01); *A61B 50/30* (2016.02); *A61B 50/33* (2016.02); *A61B 50/34* (2016.02);
(Continued)

(58) Field of Classification Search
CPC .......... A61L 2/07; A61L 2/26; A61L 2202/11; A61L 2202/121; A61L 2202/122;
(Continued)

(56) References Cited

U.S. PATENT DOCUMENTS

| 2,990,948 A | 7/1961 | Zackheim |
| 4,402,407 A | 9/1983 | Maly |

(Continued)

FOREIGN PATENT DOCUMENTS

| EP | 0 908 190 | 4/1990 |
| JP | 2004-267757 | 9/2004 |

(Continued)

OTHER PUBLICATIONS

International Search Report, PCT/NZ2015/050142, dated Mar. 17, 2016.

(Continued)

*Primary Examiner* — Timothy C Cleveland
(74) *Attorney, Agent, or Firm* — Young & Thompson

(57) ABSTRACT

Disclosed is a steam sterilizer, and a single use/disposable container for use in the sterilizer and a sterilization method. The container is a rigid or semi-rigid container having a sealable elongate conduit through which steam sterilant may be introduced into the container and steam sterilant and condensate may be removed from the container. Once one or more items to be sterilized are placed in the container a cover is sealed over the mouth of the container. The steam sterilizer has a sterilization chamber adapted to receive the container and provide sterilant within and around the container. Sterilant is provided to the container via the conduit which is sealed at the end of the sterilization process.

10 Claims, 6 Drawing Sheets

(51) Int. Cl.
| | |
|---|---|
| *B65B 31/06* | (2006.01) |
| *B65B 55/18* | (2006.01) |
| *A61B 50/34* | (2016.01) |
| *A61B 50/30* | (2016.01) |
| *A61B 50/33* | (2016.01) |
| *B65B 55/02* | (2006.01) |
| *A61B 50/00* | (2016.01) |

(52) U.S. Cl.
CPC ............... *A61L 2/26* (2013.01); *B65B 31/06* (2013.01); *B65B 55/027* (2013.01); *B65B 55/18* (2013.01); *A61B 2050/005* (2016.02); *A61L 2202/11* (2013.01); *A61L 2202/121* (2013.01); *A61L 2202/122* (2013.01); *A61L 2202/123* (2013.01); *A61L 2202/182* (2013.01); *A61L 2202/24* (2013.01)

(58) Field of Classification Search
CPC ......... A61L 2202/123; A61L 2202/182; A61L 2202/24; A61B 50/30; A61B 50/33; A61B 50/34; A61B 2050/005; B65B 31/06; B65B 55/027; B65B 55/18
See application file for complete search history.

(56) References Cited

U.S. PATENT DOCUMENTS

| | | |
|---|---|---|
| 4,671,943 A | 6/1987 | Wahlquist |
| 5,097,865 A | 3/1992 | Riley |
| 5,140,136 A | 8/1992 | Fellows et al. |
| 5,248,486 A | 9/1993 | Matsuoka et al. |
| 5,271,893 A | 12/1993 | Newman |
| 5,350,064 A | 9/1994 | Schneck |
| 6,018,143 A | 1/2000 | Check |
| 6,444,961 B2 | 9/2002 | Clothier et al. |
| 6,519,835 B1 | 2/2003 | Von Arx et al. |
| 6,715,628 B1 | 4/2004 | Nichols et al. |
| 7,164,852 B2 | 1/2007 | Cazzini et al. |
| 7,942,264 B2 | 5/2011 | Friderich et al. |
| 8,241,587 B2 | 8/2012 | Friderich et al. |
| 8,261,963 B2 | 9/2012 | Gaynor et al. |
| 8,418,872 B2 | 4/2013 | Smith |
| 8,518,341 B2 | 8/2013 | Friderich et al. |
| 8,623,289 B2 | 1/2014 | Cesa et al. |
| 2002/0119074 A1 | 8/2002 | McGowan, Jr. |
| 2004/0062693 A1 | 4/2004 | Lin et al. |
| 2006/0011596 A1 | 1/2006 | Sharp et al. |
| 2008/0236631 A1 | 10/2008 | Lin et al. |
| 2009/0217626 A1 | 9/2009 | Kemp et al. |
| 2010/0154353 A1* | 6/2010 | Cesa .................. A61L 2/26 53/167 |
| 2010/0158751 A1 | 6/2010 | Friderich et al. |
| 2010/0158753 A1 | 6/2010 | Friderich et al. |
| 2012/0047850 A1 | 3/2012 | Kemp et al. |
| 2012/0057810 A1 | 3/2012 | De Klerk et al. |
| 2012/0152289 A1 | 6/2012 | Smith et al. |
| 2012/0156092 A1 | 6/2012 | Sujiver |

FOREIGN PATENT DOCUMENTS

| | | |
|---|---|---|
| JP | 2012-513814 | 6/2012 |
| WO | WO 79/00077 | 2/1979 |
| WO | 2010/073197 | 7/2010 |
| WO | WO 2010/134893 | 11/2010 |
| WO | WO 2014/002938 | 1/2014 |

OTHER PUBLICATIONS

Written Opinion, PCT/NZ2015/050142, dated Mar. 17, 2016.
European Examination Report for European Application No. 15 791 792.3 dated Nov. 28, 2018.
Japanese Office Action for Application No. 2017-513806 dated Jul. 5, 2019 with English translation provided.

\* cited by examiner

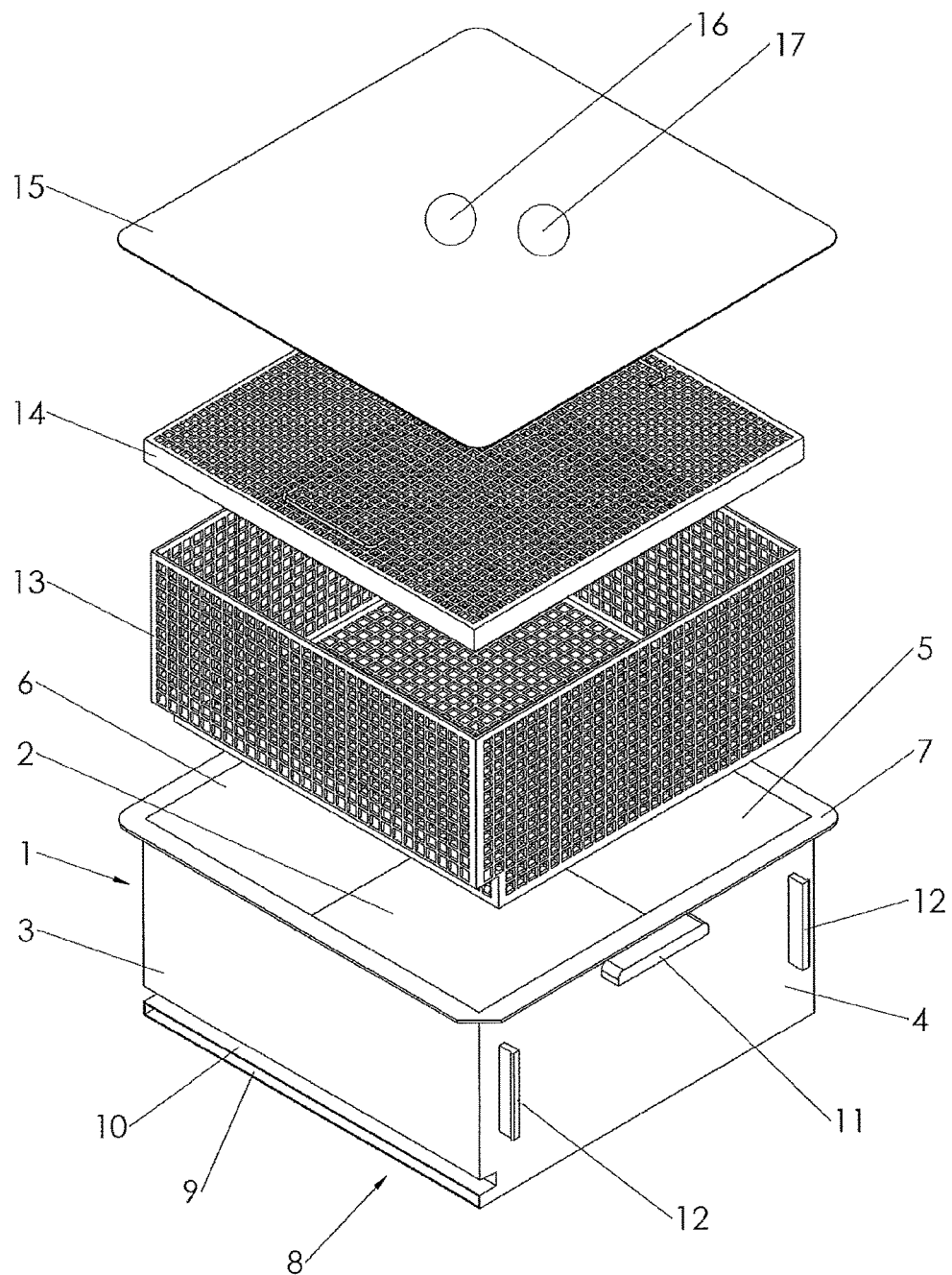
Figure 1
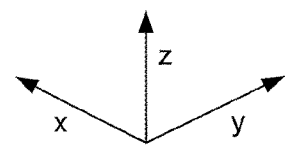

STERILISATION CONTAINER, METHOD OF STERILISATION AND STERILISATION APPARATUS

FIELD OF THE INVENTION

The present invention relates to a single use/disposable impervious sealable container for sterilising items that is capable of retaining a vacuum for an extended period, a sterilisation process using the container and a sterilisation system suitable for use with the container.

BACKGROUND OF THE INVENTION

In a healthcare facility it is necessary that all equipment and materials used for treating patients are safe for use; the chance of spreading infection should be minimal. As is well known, articles used in the operating room, such as surgical instruments, must be sterilised before each use.

The current steam sterilization industry best practice packaging using porous materials has a contestable and identified risk associated for the patient, by transference of infection and the risk of re-contamination of the sterilized items from airborne micro-organisms.

Currently used medical packaging (with the exception of irradiation methods) typically requires a porous section to facilitate the removal of air and the introduction and removal of sterilant and moisture. This porous section is then relied on as the barrier after processing. Variations in temperature and pressure can result in air being drawn into the sterilised article with the potential for recontamination.

Not withstanding the substantial research and investment in breathable sterile barrier systems the necessity of the barrier material to be breathable during the sterilisation process/cycle in the steriliser chamber and then conversely an impervious barrier system after sterilisation is extremely unlikely. This conflicting demand of the breathable barrier system poses a dilemma for most current products.

The dichotomy of the sterile barrier system persists in current practices and the challenge for the packaging suppliers and users is that the sterile barrier system must be porous or breathable to facilitate air removal and sterilant penetration/removal during the sterilisation process within the steriliser and then crucially at the completion of a successful sterilisation process, provide impervious protection as a viral and liquid barrier until aseptic release at point of use.

In current practice at the end of a correct sterilisation process, articles inside the steriliser chamber are sterile. The air in the room where the steriliser is installed contains dust particles, which may carry microorganisms; therefore the potential exists when taking out the load from the steriliser that it may be contaminated again.

Additionally sterile articles are usually stored for quite some time before use and moreover they are transported through the healthcare facility to the place they are to be used. It is thus obvious that when not protected the goods may be re-contaminated by the time they are used.

Articles therefore must be placed in a packaging to prevent recontamination after sterilisation and at the same time the packaging should be suitable to allow sterilisation of the articles it contains within a steriliser chamber. Packaging is essential for maintaining sterility; moreover the packaging must protect its load against damage during handling and transport.

Current practices of packaging depending on the use, storage and transportation, dictates that a sterile article should be packaged in one or more packaging layers. The inner primary packaging endeavors to prevent recontamination of the articles after sterilisation and hopes to provide an effective microbial barrier whilst it must allow the passage of air and the sterilant. The secondary layer is applied to facilitate proper storage and transport protection of the articles whilst it must allow the passage of air and the sterilant and in addition the combination of the packaging layers must allow the passage of air and the sterilant. The 'barrier' to microbiologic ingress is thus defined as a tortuous path.

The combination of the packaging layers therefore strives to function as a sterile barrier system that enables medical articles to be sterilised, maintain sterility and ensure the articles sterility until the time of use or the packaging expiry date. The ISO definition of a sterile barrier system is "a minimum package that prevents ingress of micro-organisms and allows aseptic presentation of the product at the point of use".

Due to current sterilisation practices the sterile barrier system is required to be "breathable" and sterile packaging is the single biggest challenge to successful sterilisation. Due to the requirement of the packaging to act as a barrier once sterile—it is inherently difficult to extract air, insert steam and subsequently extract the resultant condensate to leave the load dry, through this barrier system. Advances in non-woven wraps with their more effective barrier construction have contributed to compounding this problem.

Fundamental to air extraction is the rate at which the air to be removed from the pack can physically pass through the barrier. No allowance for load sizing or service (water pressure/steam supply) variance or time-based extraction is implemented. A common problem with today's sterilisers is the vacuum system is too efficient and the vacuum stages cycle faster than the air can get out through the barrier (A common symptom of this is packs 'blowing up' under vacuum). Conversely the pressure stages that are supposed to force steam into the packs are also too efficient and the steam simply cannot penetrate effectively in the time allowed due to the multiple layers (torturous path) of the porous wrap.

This very typical problem encountered with breathable sterile barrier systems is made even worse by lightly loaded cycles or mixed loads where some porous packs are in with non-porous instrument cases etc. and results in inadequate air removal, steam penetration failure and non-sterile packs within the loads.

Traditionally packaging materials were reusable but due to their inadequate microbial barrier properties most of these traditional materials do not meet the requirements for primary sterile packaging anymore. Presently non-wovens, laminated film pouches, paper bags and containers are used as primary packaging materials. These include muslin wraps, various paper wraps and non-woven wraps, or alternatively laminated film pouches or sterilisation containers. The wraps are typically secured by autoclavable tape which may become detached during processing or in the handling of a package leading to rejection of the package. An important feature of fabric is its "breathability" or the ability of the fabric construction to allow the passage of air and water vapour (i.e. steam). Current practices where breathable packaging is required to allow the passage of the sterilant (water vapour/steam) in and out of the package during the sterilisation process places huge demands on the breathable packaging at the conclusion of the sterilisation process to then act as a viral and liquid barrier to ensure impervious protection of the terminally sterile load. The sterilised package should be constructed so that it may be easily opened without the packaging contaminating the contents.

The minimum requirement of any packaging configuration is that it will maintain sterility of the package load until aseptic presentation at the point of use.

Due to the many variables sterilisation services practitioners are faced with everyday new standards are evolving and the International Organisation for Standardisation (ISO) is working globally to coordinate standards.

The most recently published standard ANSI/AAMI ISO 11607:2008 section titled "Packaging for terminally sterilised medical devices" has two parts namely; Part1: Requirements for materials, sterile barrier systems and packaging systems, and Part2: Validation requirements for forming, sealing and assembly processes. The emphasis is clearly on patient safety regardless of where or how the product is sterilised.

Packaging utilized for sterilisation and forming a barrier system for subsequent storage and transportation is typically comprised of non-woven wraps, paper and plastic pouches or rigid metal and plastic vented containers.

Rigid containers offer another option for enabling sterilisation of medical instruments and items. They are usually re-usable and come in a variety of sizes and materials.

The containers consist of a receiving body, often with a perforated base, over which perforations a filter of porous material is fitted and located in place with a retainer. A separate lid, with a similar perforated area, filter and retainer is latched and locked onto the base. The lid has a silicon seal fitted around the top for sealing to the base. The items to be sterilised are typically loaded into a removable basket or tray that is lowered into the container.

Rigid containers being reusable are susceptible to damage over time and must be carefully inspected before each use. Correct placement of the filter is essential and the filter material must be of the manufacturers approved type.

Unfortunately this visual inspection methodology is very subjective and there is no qualitative way of determining the biological barrier integrity of the locked container post sterilisation in an autoclave. Small dents in the base or lid mating areas or nicks in the seal are likely to mean the seal is unable to form a barrier. Defects in or incorrect fitment of the filters and retainers can expose the perforations and provide a path for contamination. Clinicians therefore have less confidence in the efficacy of the container's sterile barrier and the sterility of the contents the older the container gets.

Re-use requires decontamination and proper cleaning of the containers and lids. This means additional resources for the hospital both in staffing and services such as steam, water and detergents.

Servicing of the containers is an ongoing and real cost including the requirement to purchase additional containers whilst damaged containers are off site for repair.

The applicant's prior application published as WO2007/055595 discloses a sterilisation method and apparatus in which items to be sterilised may be sterilised within a plastic bag whilst the exterior of the sterilisation bag is maintained at atmospheric pressure. The applicant's prior application WO2010/093265 discloses an improved bag. The disclosure of these applications is hereby incorporated by reference.

It is an object of the invention to provide an improved sterilisation container, system and apparatus or to at least provide the public with a useful choice.

SUMMARY OF THE INVENTION

There is thus provided a rigid or semi-rigid single use/disposable container having:

a. a base and side walls of non-porous material defining a cavity for containing an item or items during steam sterilisation and isolating it from its surroundings after sterilisation;
b. a rim extending outwardly from the walls; and
c. a sealable conduit configured and arranged so that, in use, steam sterilant may be introduced into the container and steam sterilant and condensate may be removed from the container via the conduit.

There is further provided a method of steam sterilisation comprising:

a. providing a rigid or semi-rigid container having an opening for receiving an item to be sterilised and a sealable conduit located at or near the base of the container extending away from the container;
b. placing an item to be sterilised within the cavity;
c. applying a cover over the opening;
d. removing fluid from the container;
e. introducing steam sterilant into the container through the conduit and around the container to provide the required sterilisation;
f. extracting fluid in the container via the conduit; and
g. sealing the conduit.

There is also provided a steam steriliser comprising:

a. a sterilisation chamber having a cavity dimensioned to receive one or more rimmed containers to be sterilised;
b. one or more top plate adapted to clamp against each rim during sterilisation;
c. one or more ports providing a fluid path from within the chamber to the exterior of the chamber;
d. a vacuum for extracting fluid from the chamber via the one or more port;
e. a steam source for supplying steam sterilant via the one or more port; and
f. a sealing device for sealing the conduit of the container.

BRIEF DESCRIPTION OF THE DRAWINGS

The invention will now be described by way of example with reference to the accompanying drawings in which:

FIG. 1 shows an exploded view of a container, tray, tray lid and cover;

DETAILED DESCRIPTION OF A PREFERRED EMBODIMENT OF THE INVENTION

In response to the challenges encountered by those of skill in the art, and from the following description, it will be evident that the requirements listed below are desirable:

One Time Use Disposable Container

A single use container avoids the performance and maintenance issues associated with reusable containers.

Enabling Sterilisation

The packaging will allow fluid that is in the packaging to be evacuated and the sterilant or sterilising agent to be introduced to reach all surfaces of its contents.

Compatible with the Sterilisation Process

The combination of the apparatus and packaging will be able to withstand the conditions that occur during the sterilisation process such as pressure changes, high temperature and humidity.

Ensure Product Integrity and Patient Safety

The sterilisation container/sterilisation process will not affect the item(s) in any other way, which may affect the quality of the item(s) or which might endanger the patient or process on which the sterile item(s) will be used, subject to the item(s) to be processed being rated for the sterilisation temperature and pressure.

Maintaining Sterility

After taking the sealed and vacuum packed sterile load/item(s) out of the apparatus it/they will remain sterile during handling, transportation and storage until use, whilst package seal integrity is intact.

Packaging Authentication

Authentication of the packaging prior to sterilisation of item(s) is desirable to ensure an authenticated and validated sterilisation container is derived from tested and approved film to facilitate most appropriate functionality with respect to sterilisation process, sealing integrity, handling, transportation and shelf-life.

Tracking and Traceability

The apparatus and packaging may desirably process individual loads/trays with each load/tray incorporating a unique identification code written to a RFID tag or similar (attached to the load) and captured in a database to facilitate data logging of process parameters per individual package and to facilitate full tracking and traceability of individual loads throughout its lifecycle.

Indicator

Transparent sealed packaging facilitates visual verification of sterilisation process indicators.

Facilitate Aseptic Opening and Presentation

Simple opening of a sealed vacuum packed sterile load/item(s) facilitating aseptic opening and direct access to the sterile load.

Visible and Tactile Indication that Packaged has been Opened or Breached

Subjecting the package to a vacuum state whence sealed after load sterility is achieved enables immediate visible indication of package vacuum loss due to either a fault of seal integrity loss, package integrity breach or package opening under normal controlled aseptic opening of terminally sterilised package. In the event that the package has lost its vacuum as a result of a failure the package may be immediately be deemed contaminated and no longer sterile.

Figure 2:
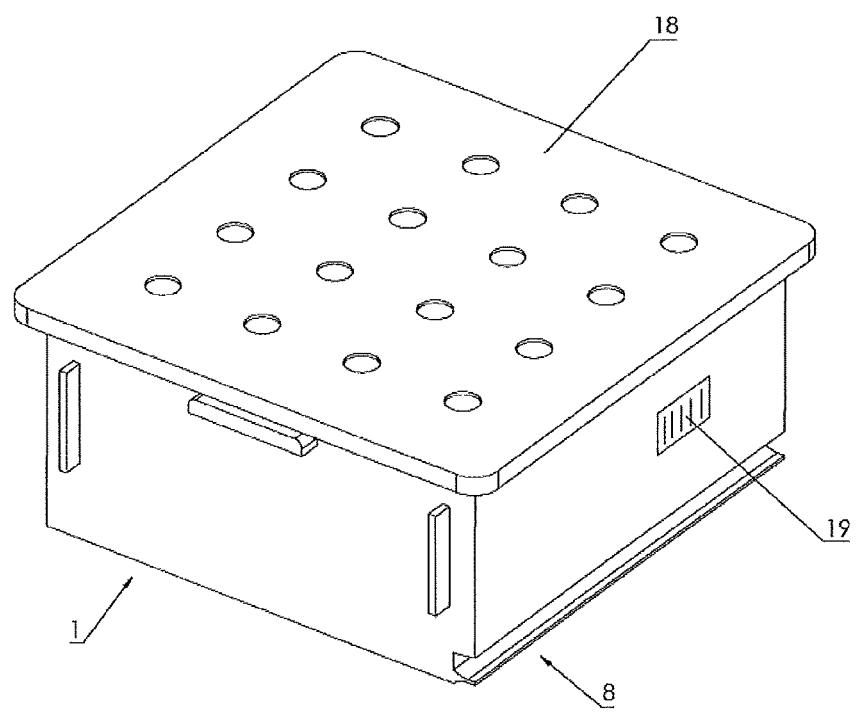
FIG. 2 shows a perspective view of a container with a container lid applied.
Figure 3:
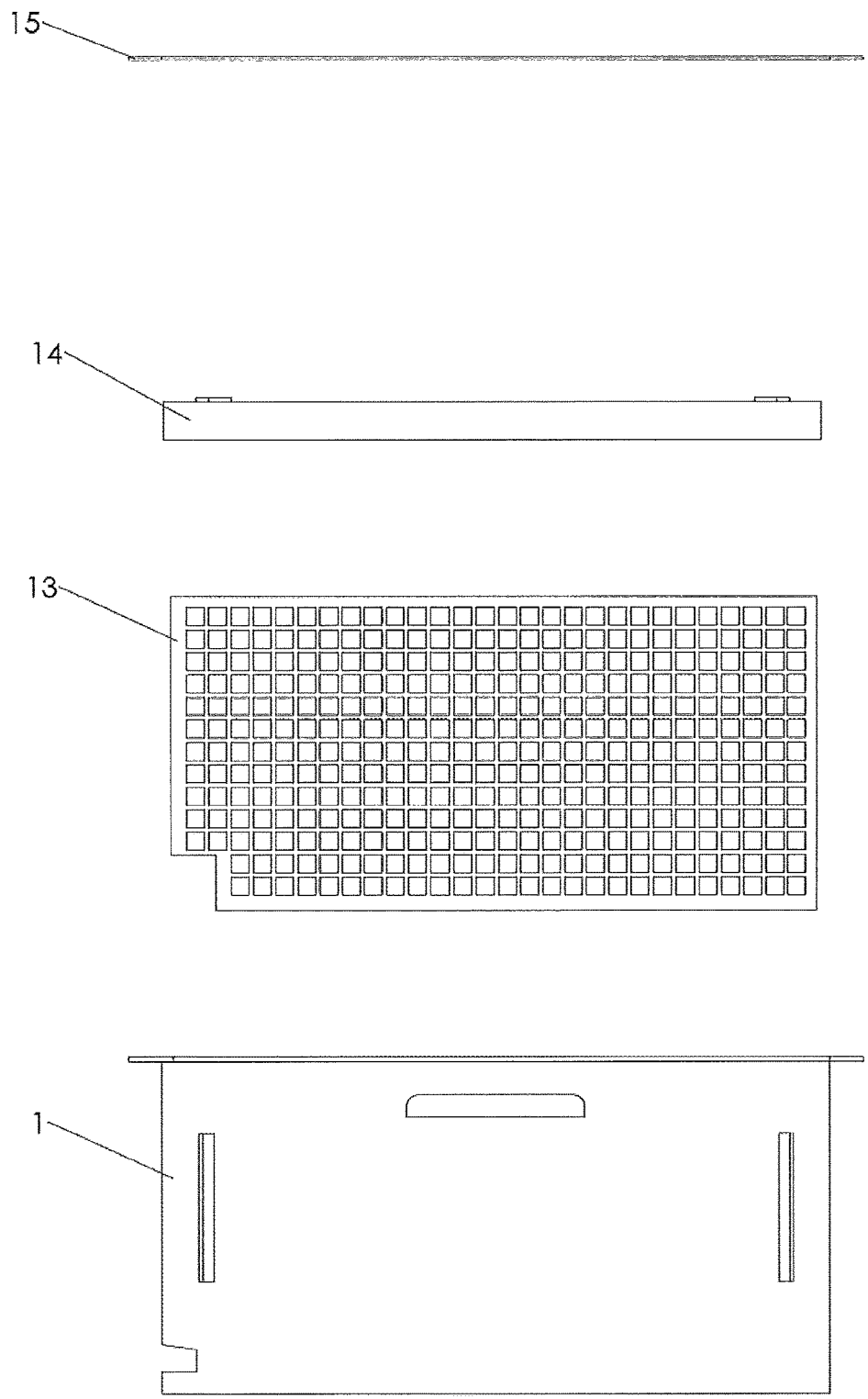
FIG. 3 shows an end view of a container, cover, tray and tray lid.

Referring now to FIGS. 1 to 3 an exemplary container will be described. Container 1 is a rigid or semi-rigid container having a base 2, and side walls 3 to 6 with a rim 7 around the top of the container. The container also includes a sealable conduit 8 having a pair of spaced apart side walls 9 and 10 forming an elongate opening which in this case extends along the entire length of side 3. The conduit 8 is configured and arranged so that, in use, steam sterilant may be introduced into the container and steam sterilant and condensate may be removed from the container via the conduit. The two opposing side walls 9 and 10 may then be sealed together to seal the conduit 8.

Conduit 8 is desirably provided at or near the base 2 of container 1 to facilitate draining of fluid (gas or liquid) from the container. Whilst in this embodiment the conduit is shown extending laterally from container 1 it could also be provided in base 2 extending downwardly. The conduit 8 is preferably elongate in cross section and generally parallel to the base 2 so as to provide steam sterilant throughout the container and provide effective draining. The conduit preferably extends along at least half the length of a side wall of the container, and preferably along the entire length, to ensure good steam distribution within the container. The conduit side walls 9 and 10 are preferably greater than 50 mm in length (the x dimension in FIG. 1), and more preferably greater than 150 mm in length. In preferred embodiments the side walls are between 50 mm and 1800 mm in length, more preferably between 150 mm and 600 mm in length. The conduit side walls 9 and 10 preferably extend at least 5 mm away from the body of the container (the y dimension in FIG. 1) to facilitate heat sealing, and more preferably greater than 10 mm. The spacing between the side walls 9 and 10 is preferably between 5 and 25 mm (the z dimension in FIG. 1). Whilst these ranges are preferred, in other applications the length could be up to or greater than 10 m. For a container that has a side wall that is 50 mm long with a spacing between conduit side walls 9 and 10 of 25 mm the aspect ratio along the conduit (viewed in direction y) will be 2:1. This is an extreme example and the aspect ratio will typically be much greater. For example for a more standard sized container having a side wall that is 150 mm long and a spacing between conduit side walls 9 and 10 of 25 mm will result in an aspect ratio of 6:1. The typical aspect ratio will be higher than this as the 25 mm spacing is greater than will typically be employed.

Handles 11 (an identical handle is provided on the opposite side) facilitate handling of the container and in combination with locating elements 12 (identical on the opposite side) assist in locating spacing elements discussed below.

Container 1 needs to be formed of a material providing an effective microbiological barrier and capable of withstanding internal steam sterilisation process temperatures. Depending on the sterilisation regime selected this may be exposure to steam at a temperature of at least 115 degrees Celsius for at least 40 minutes; a temperature of at least 121 degrees Celsius for at least 15 minutes; or a temperature of at least 138 degrees Celsius for at least 3.5 minutes. The material will also desirably withstand external steam sterilisation process temperatures of up to 180 degrees Celsius.

The container 1 may be formed of a suitable plastics material that provides the required microbial, oxygen and vapour barriers and can withstand sterilisation conditions. Suitable materials may include polypropylene (PP), linear low-density polyethylene LDPE), high density polyethylene (HDPE) and Biax Nylon (BOPA) PET-AlOx/PP (Aluminium Oxide coated PET such as Barrialox®) or EVOH.

Articles to be sterilised may be conveniently placed in perforated tray 13 with perforated lid 14 covering perforated tray 13. The tray 13 may then be placed within the container 1 and a cover 15 applied over the container 1 with the cover extending to cover at least part of rim 7 so that it may be sealed thereto.

The cover may be formed of a stretch or non-stretch material that provides the required microbial, oxygen and vapour barriers and can withstand sterilisation conditions. Certain vacuum skin packaging materials will be suitable. Thermoformable materials such as metalised stretch film or Easypeel PET-AlOx/PP (Aluminium Oxide coated PET such as Barrialox®) or EVOH may be suitable. Suitable non-stretch materials include polyethylene or polypropylene. The cover 15 may be sealed to rim 7 in a variety of ways as will be discussed below.

The cover 15 or container 1 may include a filtered vacuum release mechanism 16 to facilitate opening. The vacuum release mechanism 16 allows the ingress via a microbiological filter of external fluid to make it easier remove cover 15 from container 1. A vacuum indicator 17 may also be provided in container 1 or cover 15 to indicate that an adequate internal vacuum has been maintained up to the point of opening.

In order to maintain an effective microbial and gaseous barrier the materials used for the container 1 and cover 15 should provide a vapour barrier of less than 0.03 $g/m^2/hr$.

A rigid lid 18 may be applied over cover 15 to provide protection for cover 15 and to provide a shape suitable for stacking. The rigid lid may be provided in a non-porous form that is sealed to container 1 to provide an additional barrier as will be described below. In some applications no lid will be required.

An identification device 19, such as an RFID tag, holographic indicia, bar code, QR code etc. may be applied to the container 1, cover 15 or lid 18. This identification device may be utilised for tracking as well as for authentication of packaging prior to sterilisation.

Figure 4:
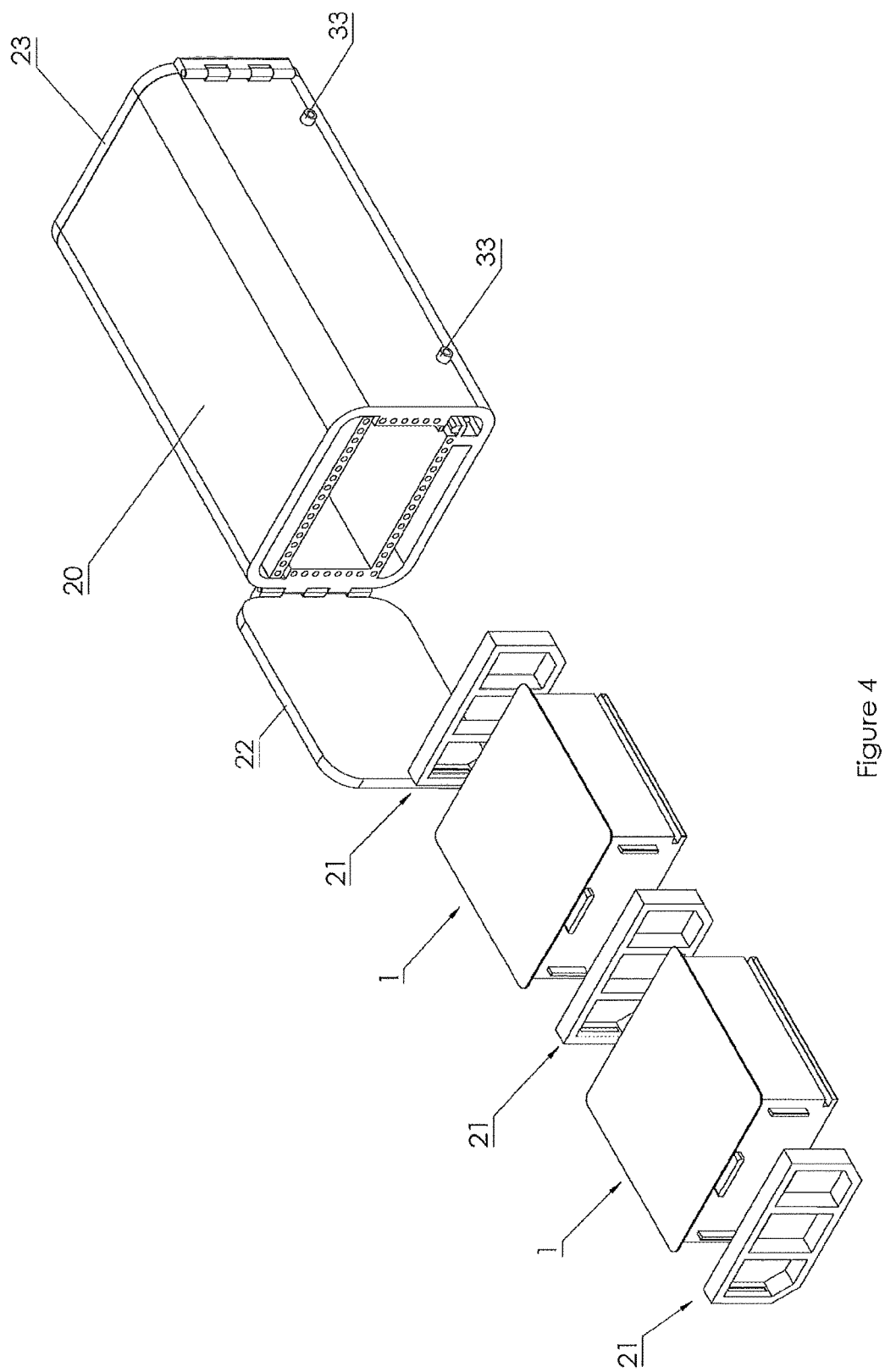
FIG. 4 shows a perspective view of a steam steriliser, a container to be sterilised and container spacers.
Figure 5:
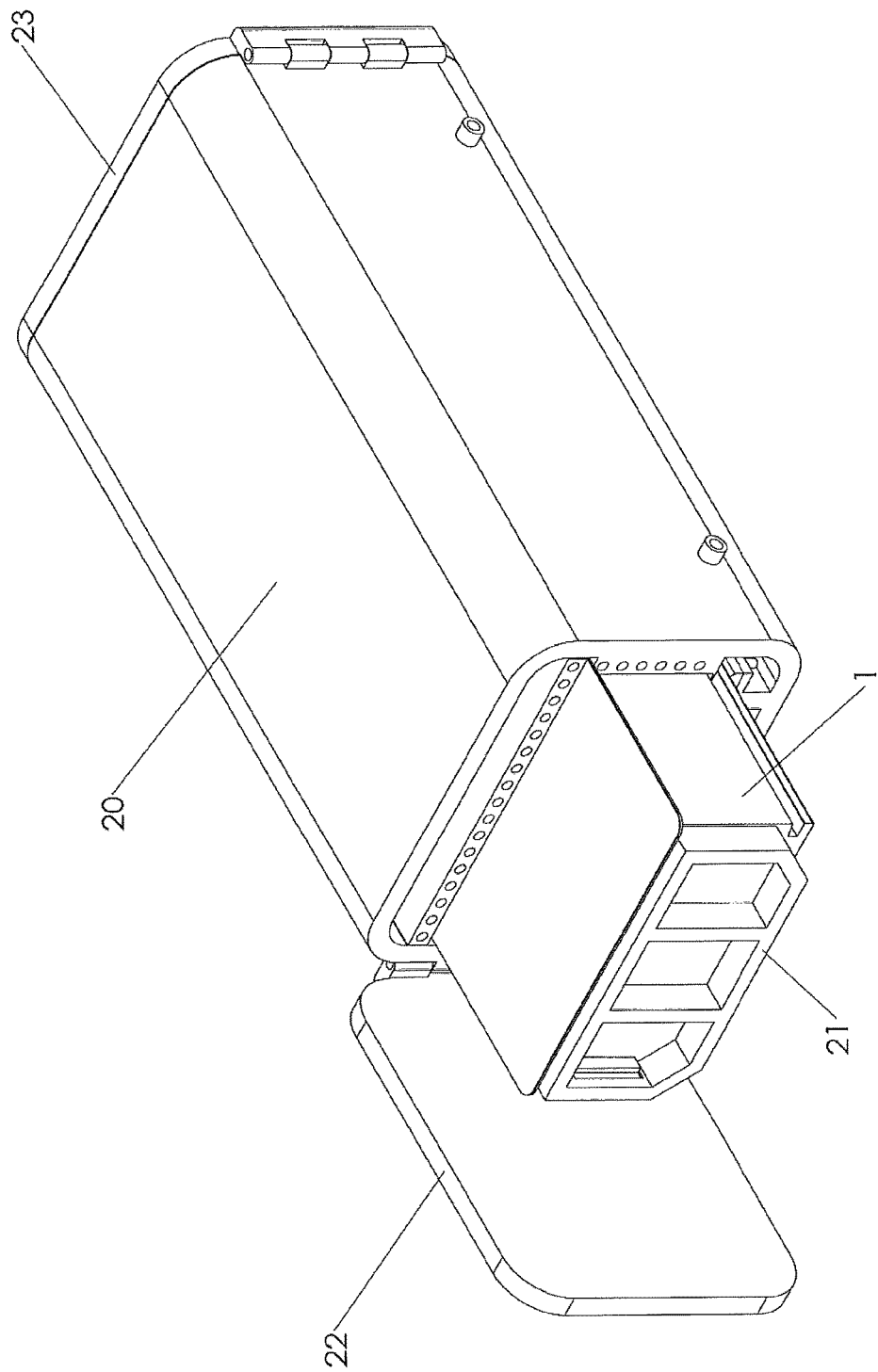
FIG. 5 shows a perspective view of a container partially within the steam steriliser.
Figure 6:
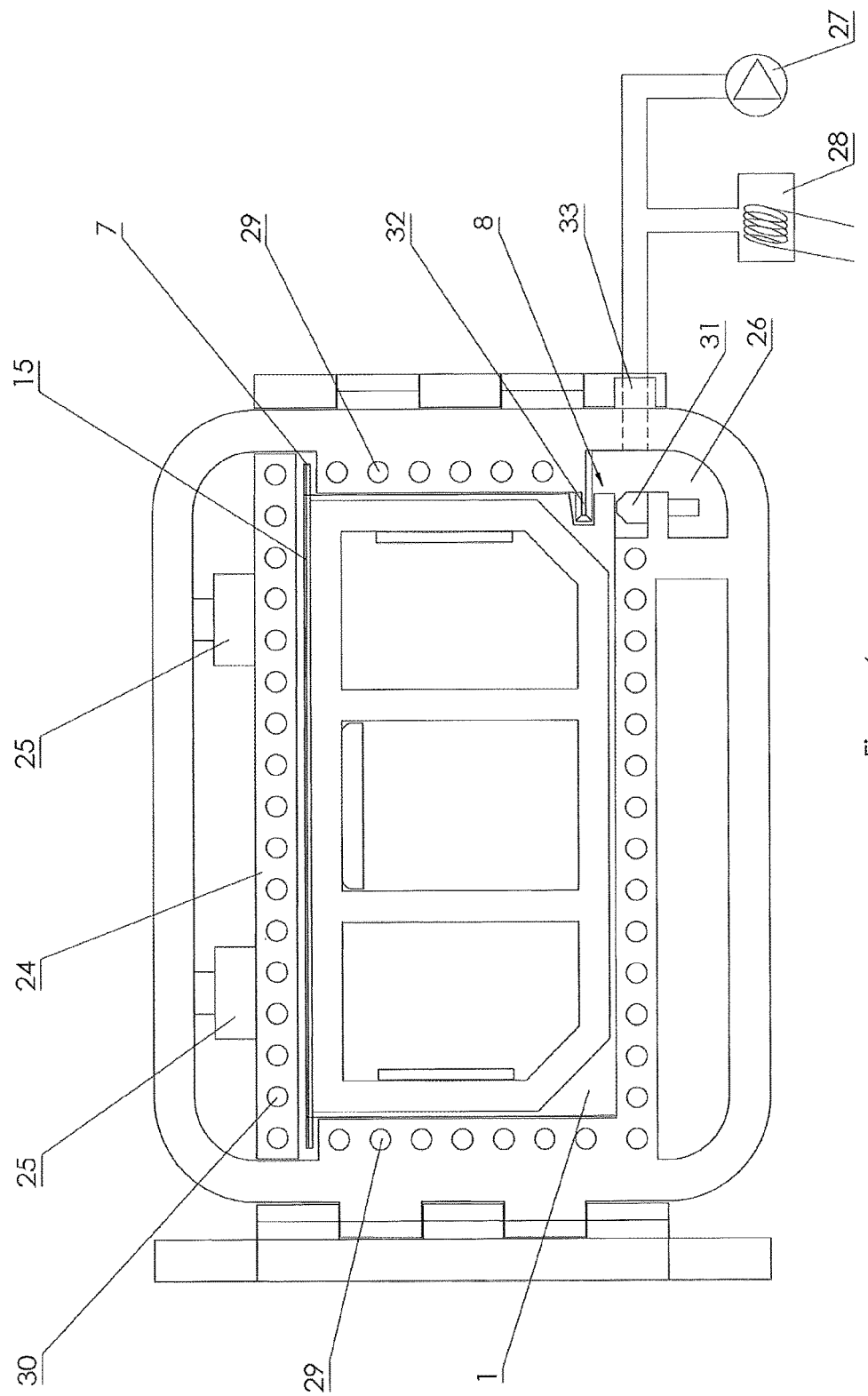
FIG. 6 shows an end view of a container within a steam steriliser.

Referring now to FIGS. 4 to 6 a steam steriliser suitable for use with the container described above is shown. The sterilisation chamber 20 has a cavity dimensioned to receive one or more containers to be sterilised. As seen in FIG. 4 a plurality of containers 1 may be sterilised at the same time. It will be appreciated that containers of different sizes may be sterilised simultaneously in the same sterilisation chamber so that a range containers of different size may be provided to accommodate different loads. Spacers 21 are placed between and at either end of containers 1 and locate with handles 11 and locating elements 12. The spacing elements provide a suitable anvil at the ends of the containers to enable the top plate 24 to clamp cover 15 against the rim 7. Doors 22 and 23 are provided at either end of chamber 20 so that containers may be fed in at one end and out the other. Of course just a single door could be provided and the containers could be fed in and out through the same door.

FIG. 5 shows a container with spacer 21 attached being fed into chamber 20. Referring now to FIG. 6 a cross-sectional view shows a container within sterilisation chamber 20. Once containers 1 are properly located within sterilisation chamber 20 the doors 22 and 23 are closed and the sterilisation chamber is sealed from the external atmosphere. A top plate 24 is then forced against cover 15 so that cover 15 is clamped to rim 7. The cover 15 may be sealed to container 1 prior to steam sterilisation but may also be sealed to rim 7 when the top plate 24 forces the cover 15 and rim 7 together.

The cover 15 may be secured to the rim 7 of container 1 either prior to entering sterilisation chamber 20 or within sterilisation chamber 20 using a number of techniques including by an adhesive (self bonding adhesive or a pressure adhesive), welding (e.g. heat sealing, ultrasonic welding, microwave welding or laser welding) or other suitable methods.

The sterilisation chamber 20 includes a port 26 providing a fluid path via conduit 33 from within the chamber to a vacuum 27 for extracting fluid from the chamber and a steam source 28 for supplying steam sterilant via the port 26. Port 26 extends along almost the entire length of sterilisation chamber 20 to mate with conduit 8 of container 1. The mating is sufficiently loose that there is a fluid path from port 26 to the exterior of container 1 also.

In the first stage of sterilisation identification device 19 may be read to ensure the container has a valid ID. After validation a vacuum 27 is activated and extracts fluid from within and around container 1. Providing conduit 8 at or near the base of container 1 facilitates the removal of liquids from container 1.

In the next stage the vacuum 27 is deactivated and steam source 28 supplies steam to port 26 and via conduit 8 to container 1 so that the entire contents of container 1 are exposed to steam sterilant. Due to the loose coupling between port 26 and conduit 8 the exterior of container 1 is also exposed to steam sterilant. Steam is also supplied to channels 29 and 30 (only one of each indicated) to heat the base and side walls of sterilisation chamber 20 and top plate 24. Due to the close contact between the side walls of the sterilisation chamber 20 and top plate 24 this ensures that there is effective thermal contact with the container.

Different sterilisation regimes may be used depending upon the requirements of a particular application and the materials employed. There is a trade off between material cost and the time required to perform sterilisation. Preferred sterilisation regimes are:

1. providing steam sterilant of a temperature of at least 115° C. to the interior of the container for at least 40 minutes.
2. providing steam sterilant of a temperature of at least 121° C. is supplied to the interior of the container for at least 15 minutes.
3. providing steam sterilant of a temperature of at least 134° C. is supplied to the interior of the container for at least 3.5 minutes.

At the completion of steam sterilisation, steam source 28 is closed and vacuum source 27 connected to port 26 to extract fluid from container 1 and its surrounds. Again having conduit 8 located at or near the base of container 1 facilitates the extraction of liquid condensate from the container 1.

Once a required vacuum is achieved conduit 8 is sealed. In this embodiment heat sealing is performed by heat sealing device 31 being heated and forced against anvil 32 to seal the conduit 8 of container 1 so that the container is entirely sealed from the external atmosphere. Whilst heat sealing is shown in this embodiment other techniques to seal conduit 8 include ultrasonic welding, adhesive bonding or mechanical closure using a suitable clamping mechanism.

Once the container is sealed a door or both doors 22, 23 of sterilisation chamber 20 may be opened and the container removed. A rigid lid 18 may then be placed over the cover 15 and secured to container 1 to facilitate stacking and transport. The rigid lid 18 may also be sealed to the container 1. This may be performed in an inert gas (e.g. Nitrogen) environment maintained at or above atmospheric pressure when the lid is sealed to the container. This provides an additional inert barrier should there be any failure with the cover seal.

There is thus provided a non-porous single use impervious and puncture resistant sealable container for steam sterilisation that is capable of retaining a vacuum for an extended period and providing an effective microbiological barrier.

By providing a rigid container in a lightweight disposable plastic form with the contents sealed in a partial vacuum the barrier integrity status can be immediately determined by visual and tactile confirmation of vacuum remaining therein.

The container may be transparent and constructed of a plastics material that is able to withstand steam processing temperatures of up to 180° C. without degrading, losing shape or structural integrity.

There is thus provided a container that is easy to use, stackable, allows simple article loading, continuous push through processing of containers and easy opening by virtue of the vacuum release mechanism and easily removed cover. The integrity of vacuum is also easily determined by visual inspection of packaging or of an indicator.

The container facilitates thorough sterilisation due to effective drainage through the conduit, good contact with the heated walls of the steam steriliser, and effective circulation of sterilant within the container.

The non-porous (non-contestable) barrier provides extended shelf life and the ability to withstand pressure and temperature variations during storage or transport without ingress of contamination.

Due to the steam steriliser providing steam sterilant within and around the container pressure differential avoided allowing the use of a wider range of materials such as an easy peel cover. The steam steriliser design also allows sterilisation to be performed on conventional or hybrid packaging (with containers and pouches).

A single fluid supply to both the container and sterilisation chamber simplifies the steam steriliser design and improves steam steriliser space utilisation.

While the present invention has been illustrated by the description of the embodiments thereof, and while the embodiments have been described in detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the applicant's general inventive concept.

What we claim is:

1. A single-use rigid or semi-rigid single use/disposable container having:
   a. a base and side walls defining a cavity for receiving an item to be sterilized;
   b. a rim extending outwardly from the side walls of the container; and
   c. a sealable conduit integrally formed with the base or one of the side walls of the container,
   the sealable conduit providing a direct passage through the base or the one of the side walls of the container to the cavity,
   the sealable conduit being elongate in cross section at the base or one of the side walls of the container,
   the sealable conduit being configured and arranged to allow, when a cover is secured to the rim in use, steam sterilant to be introduced into the container and steam sterilant and condensate to be removed from the container between an exterior of the container and an interior of the container by direct passage through the base or the one of the side walls of the container via the conduit,
   wherein the sealable conduit is formed by two opposing side walls that extend outwardly from the base or the one of the side walls of the container with which the sealable conduit is integrally formed,
   wherein said container is a single-use container.

2. A container as claimed in claim 1 wherein the sealable conduit is provided at, near or in the base to facilitate draining of the container.

3. A container as claimed in claim 1 wherein the aspect ratio of the cross-section of the sealable conduit is greater than 2:1.

4. A container as claimed in claim 1 wherein the two opposing side walls of the sealable conduit are greater than 50 mm in length and are configured to be sealed together to thereby seal the elongated cross section to the sealable conduit.

5. A container as claimed in claim 4 wherein the spacing between the side walls of the sealable conduit is between 5 mm and 25 mm.

6. A container as claimed in claim 4 wherein the sealable conduit side walls extend outwardly from the body of the container more than 5 mm, and wherein the aspect ratio of the elongate cross section is at least 6:1.

7. A container as claimed in claim 1 wherein the sealable conduit extends along more than half the length of one of the side walls of the container.

8. A container as claimed in claim 1 formed of a material capable of withstanding internal steam sterilisation process temperatures of at least 115 degrees Celsius for at least 40 minutes.

9. A container as claimed in claim 1 formed of a material selected from polypropylene (PP), linear low-density polyethylene (LDPE), high density polyethylene (HDPE), Biax Nylon (BOPA) PET-AIOx/PP (Aluminium Oxide coated PET) or EVOH.

10. A container as claimed in claim 1 including a cover fused to the rim of the container formed of a thermoformable material or a non-stretch plastics material.

* * * * *